United States Patent [19]

Heuscher et al.

[11] 4,333,145

[45] Jun. 1, 1982

[54] METHOD OF HIGH RESOLUTION PARTIAL AREA SCAN INVOLVING CONCENTRATED HIGH DENSITY MATERIAL OUTSIDE THE PARTIAL AREA

[75] Inventors: Dominic J. Heuscher, Aurora; Roland W. Carlson, Lyndhurst, both of Ohio

[73] Assignee: Technicare Corporation, Solon, Ohio

[21] Appl. No.: 98,431

[22] Filed: Nov. 29, 1979

[51] Int. Cl.³ .................... G01N 23/00; G01T 1/20
[52] U.S. Cl. ................... 364/414; 250/362; 250/445 T; 358/111; 364/515
[58] Field of Search .............. 364/414, 515, 572; 250/358 R, 360, 362, 445 R, 445 T; 358/96, 111, 166

[56] References Cited

U.S. PATENT DOCUMENTS

| | | | |
|---|---|---|---|
| 3,696,249 | 10/1972 | Bowker | 358/96 |
| 3,809,904 | 5/1974 | Clarke et al. | 250/358 R |
| 3,944,830 | 3/1976 | Dissing | 250/358 R |
| 4,069,422 | 1/1978 | Hounsfield | 250/360 |
| 4,149,248 | 4/1979 | Pavkovich | 364/515 |
| 4,205,375 | 5/1980 | Inouye et al. | 364/414 |
| 4,217,641 | 8/1980 | Naparstek | 250/445 T |
| 4,223,384 | 9/1980 | Hounsfield et al. | 250/445 T |

OTHER PUBLICATIONS

Ethier et al.; "Development of High Resolution Computed Tomography of the Spinal Cord"; Dept. of Radiology-Montreal Neur. Hosp.-Jnl. of Comp. Ass. Tomography; vol. 3, No. 4, Aug. 1979; pp. 433-438.

*Primary Examiner*—Errol A. Krass
*Attorney, Agent, or Firm*—Michael A. Kaufman

[57] ABSTRACT

A method of minimizing a streaking effect found in reconstructed images obtained from high resolution CT scanning of a small scan circle that corresponds to a limited region of interest, such as portions of the spinal cord of a patient, particularly in scans that include concentrated high density material, such as bone, situated outside the small scan circle. The approximate range of view angles that will project bone from outside the limited region of interest is determined. Detectors corresponding to the determined region are selected out. The projection data acquired by the selected detectors is filtered. The filtering is accomplished by convolving the projection data with a preselected filter function or in machine implemented form by passing the electrical signal representing the projection data through a low pass filter.

10 Claims, 8 Drawing Figures

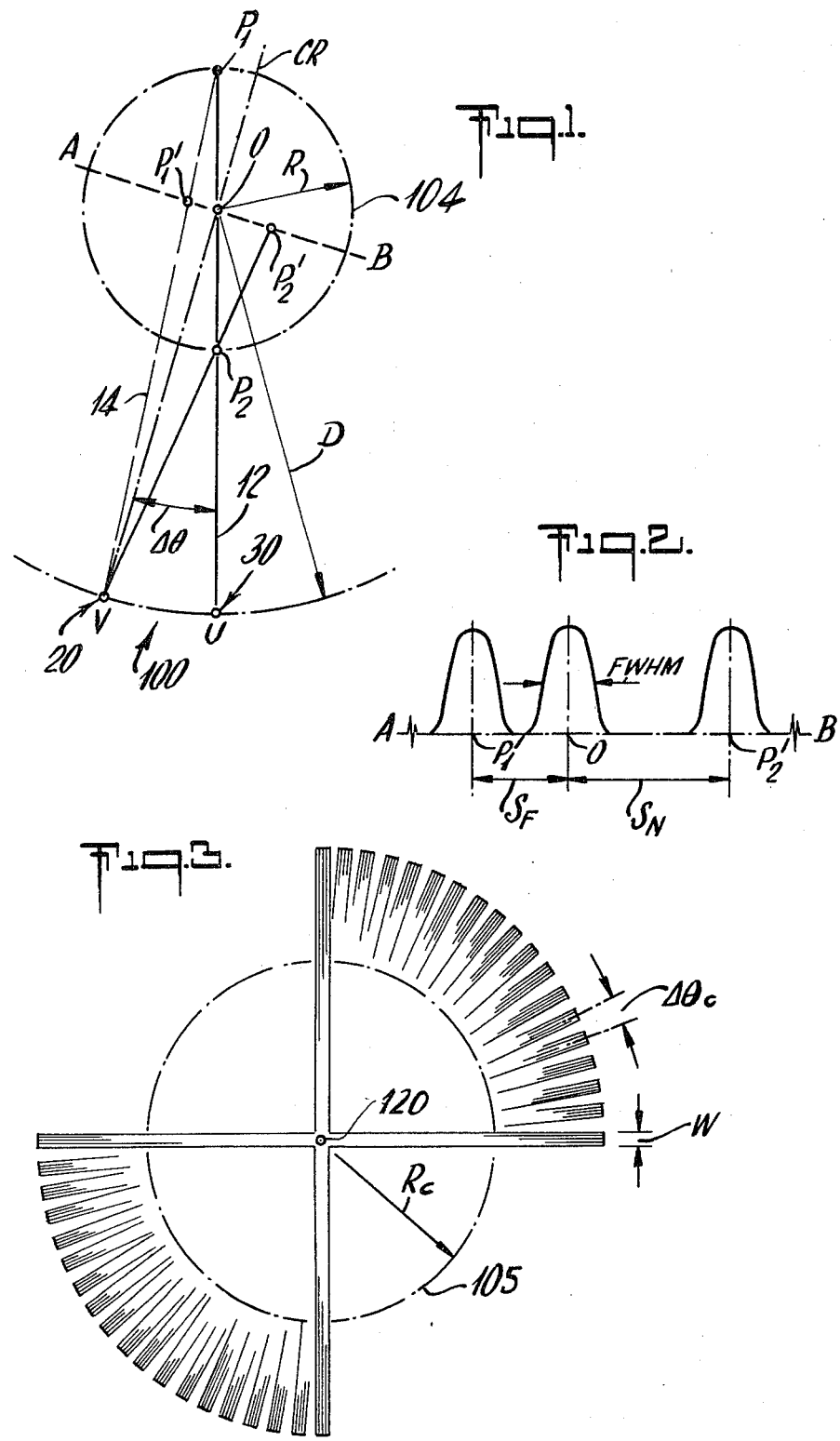

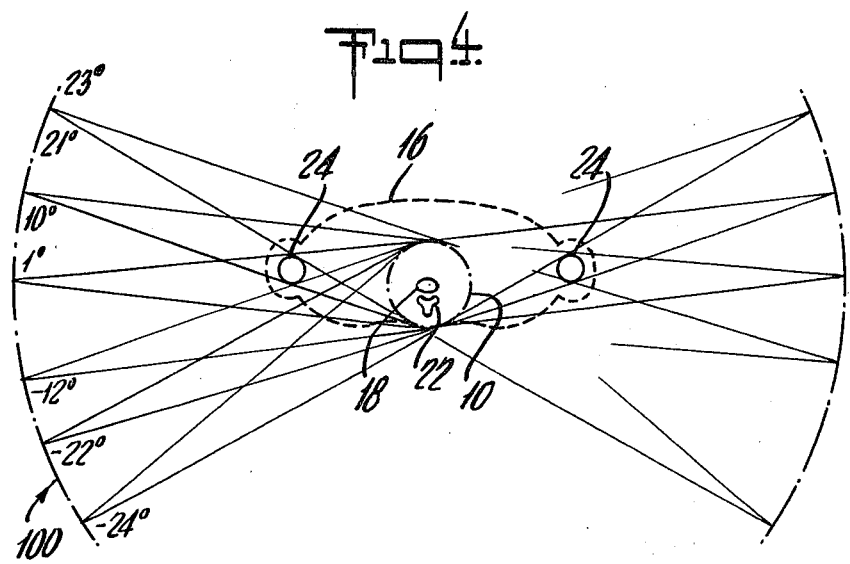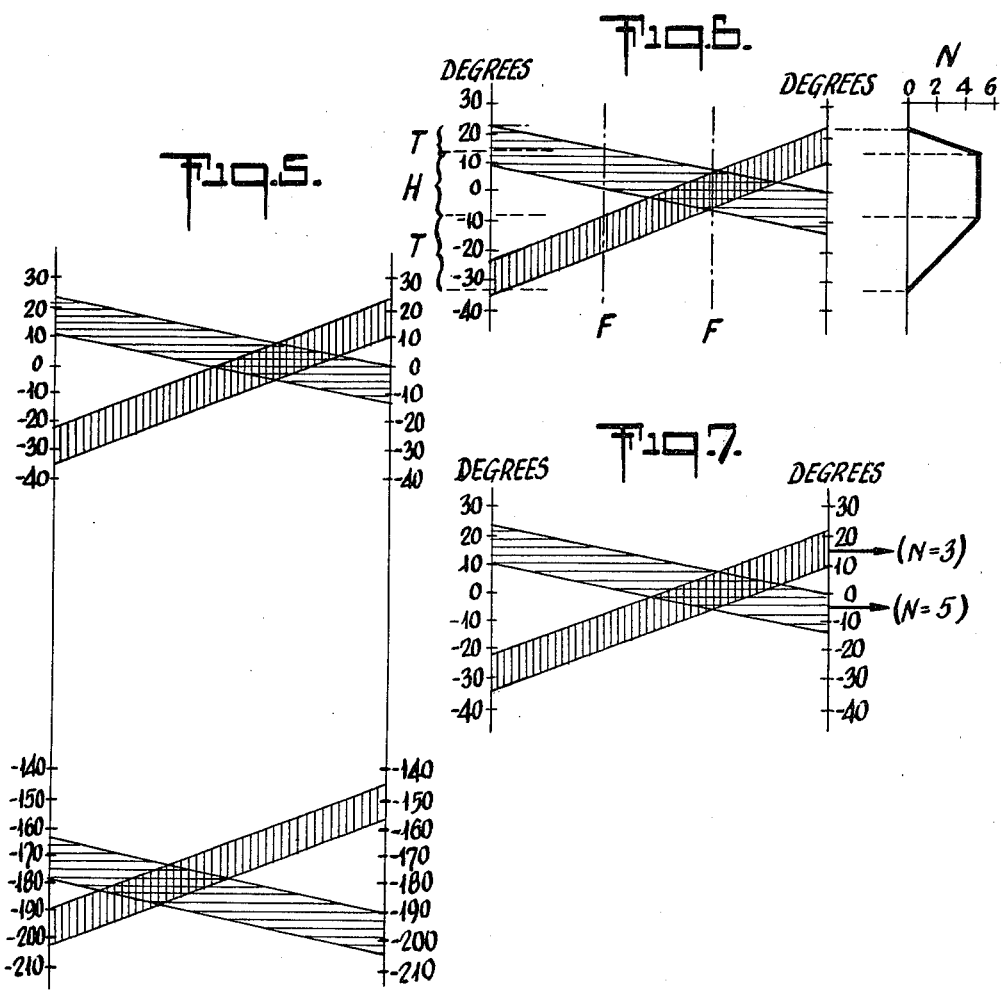

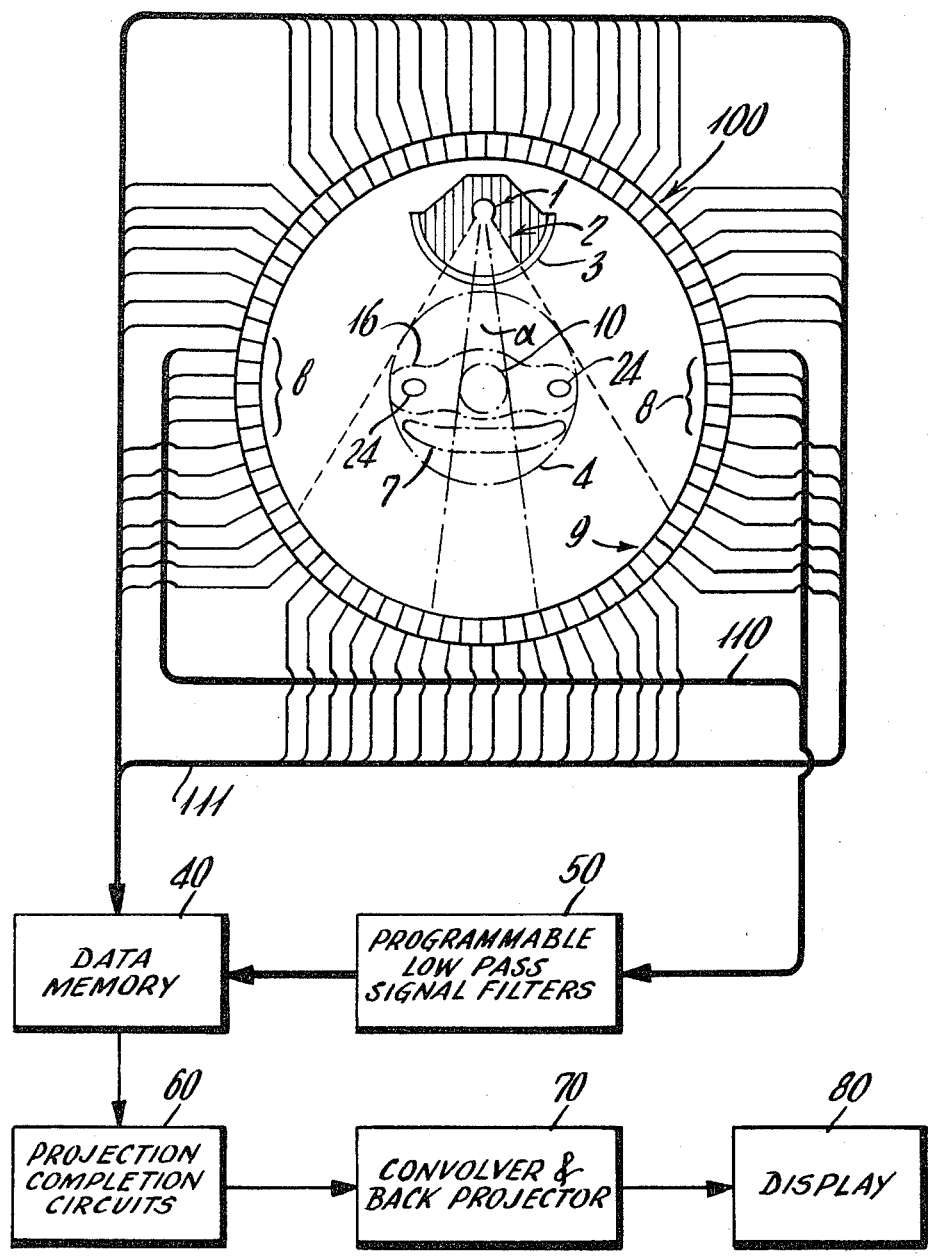

METHOD OF HIGH RESOLUTION PARTIAL AREA SCAN INVOLVING CONCENTRATED HIGH DENSITY MATERIAL OUTSIDE THE PARTIAL AREA

TECHNICAL FIELD

This invention relates to a method of eliminating or at least substantially minimizing a streaking artifact observed in high resolution computed tomography (CT) scans of a small area of interest such as the spine in the vicinity of bones lying within a scan, but outside the imaged region.

BACKGROUND ART

State of the art CT body scanners are being modified to produce high resolution images of such traditionally difficult areas as the spine. R. Ethier et al. in 3 Journal of Computer Assisted Tomography 433 (August, 1979) have reported high resolution CT images of lesions in the spinal cord.

Such limited regions of anatomical interest as the spinal cord lie well within the total body portion of a patient positioned within the scanning apparatus. To permit higher resolution in the area of diagnostic significance, the apparatus is made to "focus" on a scan circle smaller than one that would include the entire body section. Accordingly, some portions of the body section will be outside the small scan circle or the "projection" used to reconstruct the image. Acceptable methods of reconstruction require some information from the region external to the small scan circle. There are several techniques for the "completion" of such incomplete or "truncated" projections. See, for example, the copending application, assigned to the assignee of the present invention, Ser. No. 99,067; filed Nov. 29, 1979, for "Projection Completion Method Of Partial Area Scan".

Concentrated high density material, such as bone, situated outside the small scan circle is not considered in previous projection completion methods. Hence, such concentrated masses produce artifacts in the form of streaking in the region of interest. In high resolution spine scanning, this artifact was first noticed when the arms were included in the slice. Having the patient hold the arms overhead eliminated the artifact. However, when the scan included the shoulders the artifact returned. The shoulders, of course, cannot easily be removed from the slice. In addition, in some cases it is not very practical to have the patient hold the arms overhead. This streaking artifact can affect substantially the diagnostic value of images obtained from relatively small regions of interest such as the spine.

DISCLOSURE OF THE INVENTION

We have discovered a method of eliminating or at least substantially minimizing this streaking artifact with minimal loss of resolution resulting in high resolution reconstruction of partial area projections in the presence of substantial dense material outside the region of interest. The present method is compatible with known projection completion methodologies, in particular, with the one referred to hereinabove, as well as being compatible with known reconstruction techniques involving backprojection and convolution.

In a preferred embodiment, the method of minimizing the effect on a reconstructed image of concentrated high density material, such as bone, situated outside a limited region of interest defined by a small scan circle comprises the step of determining the approximate range of view angles of the small scan circle which include a projection contribution from the concentrated high density material from outside the small scan circle. The method according to the preferred embodiment further comprises the step of selecting those detectors used in the scanning which correspond in placement to view angles having an external high density material contribution and the step of filtering the projection data acquired by the selected detectors.

In the preferred embodiment, the projection data referred to in the filtering step is convolved with a preselected filter function. The preselected filter function is preferably of variable width as a function of view angle.

In an alternate embodiment, the method is machine implemented wherein said filtering step comprises passing signals representing the projection data acquired by the selected detectors through a low pass filter thereby eliminating high frequency components thereof.

BRIEF DESCRIPTION OF THE DRAWINGS

FIG. 1 is a geometric representation of a circle of radius R disposed within the larger circle defined by the detectors of a CT scanner.

FIG. 2 is a graphical display of selected projections illustrated in FIG. 1.

FIG. 3 illustrates backprojection of positive portions of convolved beams.

FIG. 4 is a sectional diagram of the outline of the thorax and shoulder and the small scan circle of FIG. 1 therewithin surrounding the limited region of interest.

FIG. 5 diagrammatically illustrates the degree range wherein the shoulder projections appear as shown in FIG. 4.

FIG. 6 is a diagram which illustrates the application of a variable width equal weighted filter used for Filter I.

FIG. 7 is a diagram which illustrates the application of medium and heavy equal weighted filters used for Filter II.

FIG. 8 is a schematic block diagram illustrating the present method in machine implemented form.

BEST MODE FOR CARRYING OUT THE INVENTION

FIG. 1 illustrates the mechanism of the artifact. Point V represents a detector 20, one of a plurality of detectors (two represented) 9 (see FIG. 8) disposed equiangularly about detector circle 100. The position of detector 20 is defined by its angular displacement $\Delta\theta$ from the normal, represented by centerline 12 emanating from point U which represents detector 30.

Points P1 and P2 located on the perimeter of circle 104 represent origins of the source of artifacts viewed by detector 20. These two points are disposed along center line 12 which intersects isocenter 0 of circle 104. From the perspective of detector 20, point P1 is on the far side of isocenter 0 while point P2 is on the near side thereof.

In the reconstruction process all points in this view will be projected to data line AB. The data line AB is normal to central ray CR which intersects point V and isocenter 0.

FIG. 2 shows the projection of information from points P1, 0, and P2 onto the data line AB. Source width, source motion, and detector aperture combine to produce an effective point spread function (PSF) for each of the three data points P1, 0, and P2. The three PSFs are shown centered on P1', 0, and P2', respectively. The full width at half maximum (FWHM), i.e. the width of the projection function at half its amplitude, is indicated on FIG. 2. Since the points are separated by a distance greater than the FWHM, they cannot blend into a uniform distribution.

Considering now only point P1, the view from detector 30 produces a backprojected ray along line 12 through the isocenter 0. The adjacent view of point P1 from detector 20 produces a backprojected ray along line 14. In the center of a matrix of backprojections, these rays will be separated by a distance $S_F$ indicated on FIG. 2. Similarly, the above analysis for point P2 indicates that its corresponding rays will be separated by a distance $S_N$ as indicated on FIG. 2.

FIG. 3 shows the effect of backprojecting beams of finite width W about a point 120 representing the origin of an artifact. The angle between views, determined by the number of detectors utilized, is $\Delta\theta_c$. If point 120 corresponds to point P1 then $\Delta\theta_c = \Delta\theta/(1-R/D)$. However, if point 120 corresponds to point P2 then $\Delta\theta_c = \Delta\theta/(1+R/D)$. Outside a circle 105 of radius $R_c$ there will be no beam overlap. Not shown in FIG. 3 are the negative wings on each beam produced by convolution with a standard deblurring filter function. Inside the circle 105 the summation of the negative wing values cancels out the positive beam portions so the net effect is a zero field everywhere except at the point being reconstructed.

Since the views of an exterior point are incomplete in the partial area scan, the above is not absolutely true, but for practical purposes, the cancellation is quite good. However, outside the circle 105 cancellation is not complete. The spaces between the positive rays will contain negative values only and a streaking artifact results from bones situated from the center of the region of interest a distance greater than critical radius $R_c$.

The critical radius for circle 105 of radius $R_c$ is given by the following expression:

$$R_c = W/\text{Tan } \Delta\theta_c \qquad (1)$$

Inspection of this relationship shows the radius can be effectively increased by either reducing the angle $\Delta\theta$ between detectors or by increasing the beam width W. The former requires an increased number of detectors. That is a costly proposition and one that entails increased maintenance. Alternatively, increasing the beam width W can be effectively and simply achieved, however, by low pass filtering of the data in those views producing the artifact. The effect of the low pass filter is to effectively increase the beam width, W, and thereby effectively increase the critical radius to include the area of interest. Once that is accomplished, the artifact is eliminated by the cancellation achieved during reconstruction.

The separation of the beams on the data line near the isocenter 0 is given by the following expressions:

Far side points:

$$S_F = \Delta\theta R/(1+R/D) \qquad (2)$$

where D = Radius of Detector Circle 100 and R = Radius of Circle 104

Near side points:

$$S_N = \Delta\theta R/(1-R/D) \qquad (3)$$

From these expressions the width of the low pass filter is determined.

FIG. 4 illustrates a small scan circle 10 shown within body section 16 disposed within detector circle 100. The area of diagnostic significance is fully contained within the region defined by small scan circle 10. For illustrative purposes only, the small scan circle 10, includes therewithin a section of the patient's spinal cord 18 and spinal column 22. Located well outside the scan circle 10 are bone sections 24, the sources of the artifact.

From the perspective of detector circle 100 which surrounds body section 16 and hence bone sections 24, the locations about detector circle 100 to which portions of bone sections 24 would project are determined. For reference purposes, the horizontal is denoted 0° and angular displacements therefrom in counterclockwise rotation are indicated as negative. This convention is consistently followed in the diagrammatical illustrations of FIGS. 5–7.

FIG. 5 illustrates where the shoulder projections appear based upon the example of FIG. 4. The shoulder located nearest the detectors first appears (as indicated on the left column) over the angle range 23 to 10 degrees and disappears (as indicated on the right column) over the range 1 to −13 degrees. The distant shoulder first appears on the right side of the projection data between 21 and 10 degrees and disappears between −22 and −34 degrees. A similar situation occurs 180 degrees around the scan circle with the nearest shoulder appearing between −167 and −181 degrees and disappearing between −190 and −203 degrees. The distant shoulder again appears on the right side between −146 and −158 degrees and disappears between −190 and −201 degrees.

For projection data of the near shoulder 24, an equal weighted filter of width 2.75 mm or 11 data points is sufficient to widen the discontinuities, i.e. effectively increase the critical radius such that they do not contribute to a streaking effect in the reconstructed image. Likewise, for the distant shoulder 24, a filter of width 1.75 mm or 7 data points is sufficient to cancel its effects. It is therefore only necessary to decide where in the projection data this filtering should take place. FIG. 4 shows the geometry that must be considered to determine at what view angles the shoulder projections appear. Once these angles have been determined, the regions in which the shoulder projections appear in the projection data can be outlined as shown in FIG. 5.

Two alternatives exist for processing the data: (1) Filter these regions with a filter which is variable in width as a function of view angle but constant along each projection. This filter is designated as Filter I. (2) Filter the regions with a filter which processes only those areas of the projections which contain the shoulder projections, one width for nearby shoulders, the other width for distant shoulders. This filter is designated as Filter II.

FIGS. 6 and 7 show how these filters are applied to the projection data.

Integer N takes on values between 0 and 5 as determined by the function illustrated to the right of FIG. 6 which according to the following relationship assures an odd number of filter elements:

$$\text{Number of Filter Elements} = 2N+1 \qquad (4)$$

Every projection line is filtered according to the N value given at the corresponding view angle. The region of heavy filtering H (hatched area) corresponds to projection lines filtered with N=5. The regions on either side of heavy filtering are transient regions denoted T and represented by the ramps. The symmetrical situation occurs for view angles 180 degrees from those shown in the diagram, i.e. for the projections shown in the lower portion of FIG. 5.

FIG. 7 indicates the application of alternative embodiment Filter II.

The heavy filter is applied to that portion of the projection data corresponding to projections of the nearby shoulder. The medium filter is applied to that portion corresponding to the projections of the distant shoulder. Again the symmetrical situation occurs for the projections shown in the lower portion of FIG. 5.

The advantage of Filter I is its simplicity and speed of operation. In the case in which an array processor is used for calculating the filtered output for the appropriate projections, only one call to the processor is necessary for each filter width being used, which may extend over several projection lines. For each projection line being processed by Filter II, two calls to the processor are required to filter the data. Therefore, the larger overhead for Filter II makes it a slower process. Furthermore, any misalignment of predicted shoulder projections in the case of Filter II will tend to cause streaking to appear sooner than in the case of Filter I. On the other hand, the minimal region operated on by Filter II, leads to an improved spatial resolution in the two-dimensional reconstruction. As shown in FIG. 6, Filter I can be designed to insure full elimination of streaking in the central portion of the image by appropriately positioning the region in which the heaviest filtering (N=5) is being performed. Any streaking that may occur would only occur in the periphery of the image. This allows a minimal loss of resolution while eliminating the artifact in the most important area of the image. Because of this and its speed and simplicity, Filter I is preferred to eliminate the shoulder artifact.

Finally, FIG. 8 is a system diagram of the above. A radiation, in particular, X-Ray source 1 is shown with X-ray shielding 2 provided thereabout. A collimator 3 is disposed about the source 1 with which the angle of the radiation beam emanating from the source is modified. In particular, without collimation, the radiation source beam projects at a wide angle resulting in a normal scan circle 4 within which a section of a body 16 is fully enclosed. However, for purposes of a partial area scan, the beam is collimated to an angle $\alpha$ which accommodates small scan circle 10. The shoulder portions 24 of the patient having body 16 is shown. The patient lies on a support table 7 during the diagnostic procedure.

Circumscribing the patient 16 is a plurality of detectors generally referred to as 9. These detectors are placed in equiangular relation about detector circle 100. Ordinarily, data accumulated by each of the detectors 9 are collected in Data Memory 40. A subset of the detectors 9 is a plurality of detectors 8 which "see" at least a portion of at least one of the shoulders 24 with the X-ray source 1 collimated for small scan circle 10 projection. A signal harness 110 is provided for transmitting the data accumulated by detectors 8 to Programmable Low Pass Signal Filters 50. The remaining detectors 9 are provided with conventional signal harness 111 for transmitting data accumulated by the remaining detectors 9 to the Data Memory 40. The signals processed in the Programmable Low Pass Signal Filters 50 is also transmitted to Data Memory 40 for subsequent projection completion by Projection Completion Circuits 60. Finally the completed projection is reconstructed by Convolver and Backprojector 70 and the reconstructed image is displayed by Display 80.

What is claimed is:

1. In a method of high resolution computed tomography scanning of a portion of a planar region of a patient such as a section of the spine by a CT scanner of the type having a scan circle defining an examination region, a rotating source of penetrating radiation movably mounted relative to said scan circle for subjecting the scan circle to radiation, an array of stationary radiation detectors coplanar with the path of the source, spaced about the axis of rotation of the source and positioned to receive at least some of the radiation that passes from said source and through the scan circle for producing signals indicative of the intensity of radiation impinging thereon, and processing means operatively connected with said detector array for reconstructing into a visual display said signals caused by radiation attenuation in the scan circle, wherein concentrated high density material such as bone tissue is situated within the planar region but outside the portion of interest, the improvement comprising:
   (a) emitting a divergent beam of radiation by said rotating source at an angle sufficiently large to encompass the portion of interest of the planar region of the patient and smaller than required for subjecting the entire scan circle to radiation, the common area within the angle of the beam at different positions of the rotating source defining a small scan circle corresponding to the portion of interest;
   (b) selecting from said array of detectors those detectors whose signals are altered by projections of bone tissue situated outside the small scan circle;
   (c) acquiring from said signals of said array of detectors a plurality of projections of the portion of interest of the planar slice of the patient corresponding to a plurality of angular orientations of the source about said patient, each projection representing the irradiated portion of the object as defined by said divergent beam;
   (d) filtering signals produced by said selected detectors so as to minimize errors introduced into the projections by the bone tissue situated outside the small scan circle; and
   (e) reconstructing said portion of interest of the planar region of said scanned patient from said plurality of projections.

2. A method according to claim 1 wherein said filtering step comprises:
   convolving the signals produced by said selected detectors with a preselected filter function.

3. A method according to claim 1 wherein said filtering step comprises:
   passing signals acquired by said selected detectors through a low pass filter thereby eliminating high frequency components thereof.

4. A method according to either of claims 1 or 2 wherein said filtering step comprises:
   providing variable filtering of said signals of said selected detectors.

5. A method of reducing errors in high resolution computed tomography scanning of a partial area of a planar region of a patient such as a section of the spine by a CT scanner of the type having a scan circle defining an examination region, a rotating source of penetrating radiation movably mounted relative to said scan circle for subjecting the scan circle to radiation, an array of stationary radiation detectors coplanar with the path of the source, spaced about the axis of rotation of the source and positioned to receive at least some of the radiation that passes from said source and through the scan circle for producing signals indicative of the intensity of radiation impinging thereon, and processing means operatively connected with said detector array for reconstructing into a visual display said signals caused by radiation attenuation in the scan circle, wherein said errors arise from concentrated high density material such as bone tissue situated within the planar region being scanned but outside the partial area, the scanning method including emitting a divergent beam of radiation by said rotating source at an angle sufficiently large to encompass the partial area of the planar region of the patient and smaller than required for subjecting the entire scan circle to radiation, the common area within the angle of the beam at different positions of the rotating source defining a small scan circle corresponding to the partial area, acquiring from said signals a plurality of projections of the partial area of the planar slice of the patient corresponding to a plurality of angular orientations of the source about said patient, each projection representing the irradiated portion of the object as defined by said divergent beam, and reconstructing said partial area of the planar slice of said scanned patient from said plurality of projections, the improvement characterized by:

selectively filtering signals from those detectors which receive radiation attenuated by bone tissue situated outside the partial area but within the divergent beam emitted by the rotating source to minimize errors introduced into the projections by said bone tissue.

6. An improved method according to claim 5 further comprising:

convolving the signals produced by said selected detectors with a preselected filter function.

7. An improved method according to either of claims 5 or 6 wherein said filtering comprises:

providing variable filtering of projection data of said signals of said selected detectors as a function of radiation intensity.

8. A method according to claim 5 wherein said filtering step comprises:

passing signals acquired by said selected detectors through a low pass filter thereby eliminating high frequency components thereof.

9. A high resolution CT scanner for scanning a portion of interest of a planar region of a patient such as a section of the spine which comprises:

(a) a scan circle defining an examination region;

(b) a rotating source of penetrating radiation movably mounted relative to said scan circle for subjecting the scan circle to radiation, said source adapted to emit a divergent beam of radiation of an angle sufficient to encompass the portion of interest and smaller than required for subjecting the entire scan circle to radiation, the common area within the angle of the beam at different positions of the rotating source defining a small scan circle;

(c) an array of stationary radiation detectors coplanar with the path of the source, spaced about the axis of rotation of the source and positioned to receive at least some of the radiation that passes from said source and through the scan circle for producing signals indicative of the intensity of radiation impinging thereon;

(d) filter means operatively connected to a subset of said detectors for filtering signals from those detectors which receive radiation attenuated by bone tissue situated outside the small scan circle, but within the divergent beam emitted by the rotating source; and (e) processing means operatively connected with said detector array and said filter means for reconstructing into a visual display said signals caused by radiation attenuation in the small scan circle.

10. A high resolution CT scanner according to claim 9 wherein said filter means comprises a programmable low pass filter.

* * * * *